(12) United States Patent
Agostinelli et al.

(10) Patent No.: US 11,191,612 B2
(45) Date of Patent: Dec. 7, 2021

(54) MAGNETIC MARKERS FOR SURGICAL GUIDANCE

(71) Applicant: ENDOMAGNETICS LIMITED, Cambridge (GB)

(72) Inventors: Tiziano Agostinelli, Cambridge (GB); Kevin Lorimer, Cambridge (GB); Quentin Harmer, Cambridge (GB)

(73) Assignee: ENDOMAGNETICS LTD

( * ) Notice: Subject to any disclaimer, the term of this patent is extended or adjusted under 35 U.S.C. 154(b) by 0 days.

(21) Appl. No.: 16/981,860

(22) PCT Filed: Mar. 18, 2019

(86) PCT No.: PCT/IB2019/052170
§ 371 (c)(1),
(2) Date: Sep. 17, 2020

(87) PCT Pub. No.: WO2019/180580
PCT Pub. Date: Sep. 26, 2019

(65) Prior Publication Data
US 2021/0153970 A1    May 27, 2021

(30) Foreign Application Priority Data

Mar. 23, 2018 (GB) .................................... 1804683

(51) Int. Cl.
*A61B 5/00* (2006.01)
*A61B 90/00* (2016.01)
*A61B 34/20* (2016.01)

(52) U.S. Cl.
CPC .............. *A61B 90/39* (2016.02); *A61B 34/20* (2016.02); *A61B 2034/2051* (2016.02);
(Continued)

(58) Field of Classification Search
CPC ...... A61B 2090/397; A61B 2090/3908; A61B 2090/3954; A61B 34/20; A61B 2034/2051
See application file for complete search history.

(56) References Cited

U.S. PATENT DOCUMENTS 5,079,006 A    1/1992 Urquhart
5,801,630 A    9/1998 Ho et al.
(Continued)

FOREIGN PATENT DOCUMENTS

EP    1933286    6/2008
RU    2014137163    4/2016

OTHER PUBLICATIONS

Vazquez,M. et al.; "A soft magnetic wire for sensor applications"; J. Phys D; vol. 29; (1996); pp. 939-949.
(Continued)

*Primary Examiner* — Joel F Brutus
(74) *Attorney, Agent, or Firm* — K&L Gates LLP

(57) ABSTRACT

An implantable magnetic marker comprising at least one piece of a large Barkhausen jump material (LBJ) containing at least one loop. The coiled marker is deployed to mark a tissue site in the body for subsequent surgery, and a magnetic detection system with a handheld probe excites the marker above or below the switching field required for bistable switching of the marker causing a harmonic response to be generated in a bistable or sub-bistable mode that allows the marker to be detected and localised.

20 Claims, 14 Drawing Sheets

(52) U.S. Cl.
CPC . *A61B 2090/397* (2016.02); *A61B 2090/3908* (2016.02); *A61B 2090/3954* (2016.02)

(56) References Cited

U.S. PATENT DOCUMENTS

| | | | | |
|---|---|---|---|---|
| 6,230,038 | B1* | 5/2001 | von Gutfeld | A61N 5/1049 |
| | | | | 128/899 |
| 6,337,627 | B1 | 1/2002 | Von Gutfeld et al. | |
| 10,042,013 | B2 | 8/2018 | Lips et al. | |
| 2003/0120148 | A1* | 6/2003 | Pacetti | A61M 25/09 |
| | | | | 600/421 |
| 2003/0204137 | A1* | 10/2003 | Chesbrough | A61M 5/007 |
| | | | | 600/426 |
| 2009/0211909 | A1* | 8/2009 | Nesbitt | A61L 31/18 |
| | | | | 204/487 |
| 2010/0042041 | A1* | 2/2010 | Tune | A61M 37/0069 |
| | | | | 604/60 |
| 2010/0204570 | A1* | 8/2010 | Lubock | A61B 90/39 |
| | | | | 600/426 |
| 2011/0038395 | A1 | 2/2011 | Sorkine et al. | |
| 2011/0313288 | A1* | 12/2011 | Chi Sing | A61B 8/481 |
| | | | | 600/437 |
| 2016/0354178 | A1 | 12/2016 | Mayes et al. | |
| 2017/0095315 | A1* | 4/2017 | van der Weide | A61B 90/39 |

OTHER PUBLICATIONS

Sulla, Igor et al.; "Utilizing Magnetic Microwires for Sensing in Biological Applications"; Electrical Engineering; vol. 66, No. 7; (2015); pp. 161-163.

PCT International Search Report and PCT Written Opinion for PCT International Patent Application No. PCT/IB2019/-52170 (12 pages).

\* cited by examiner

Sensing end of probe

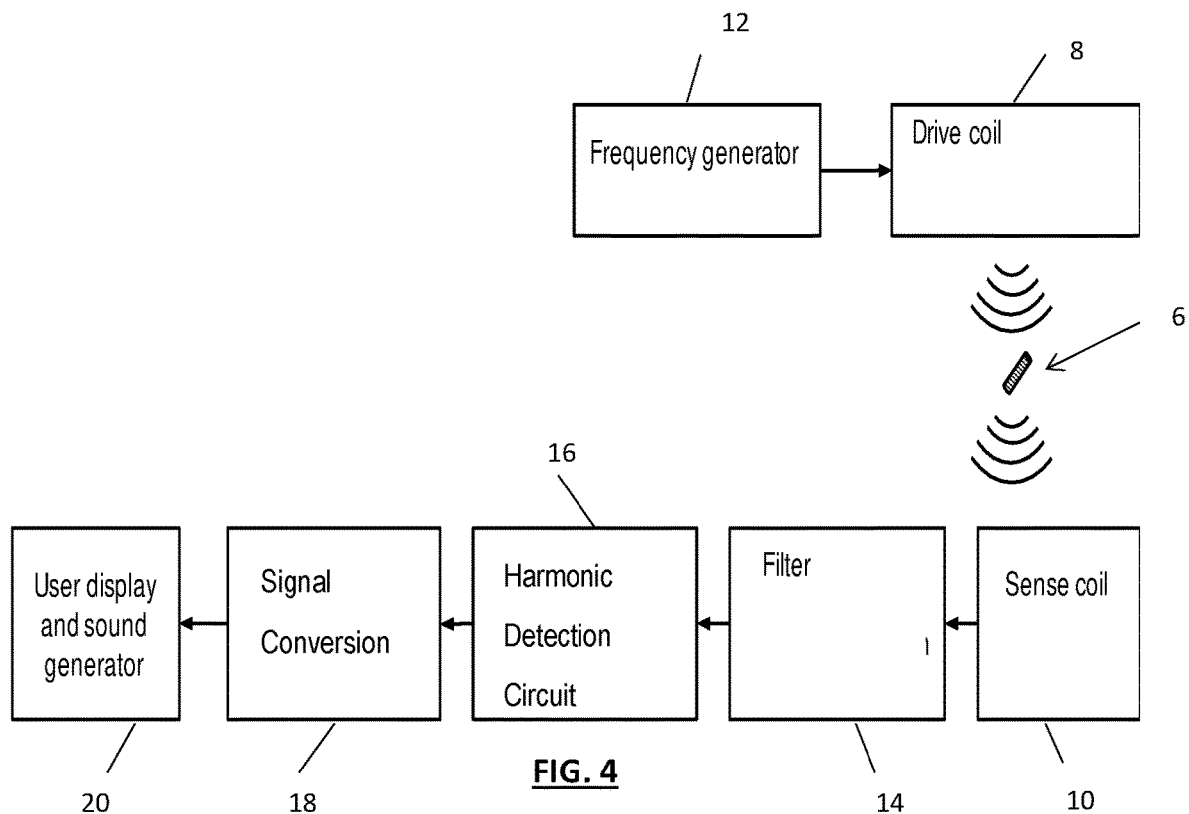
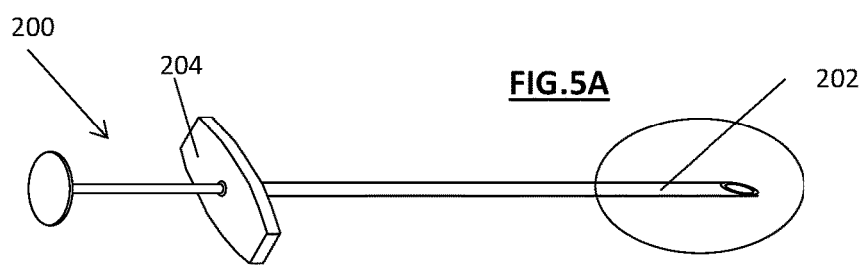
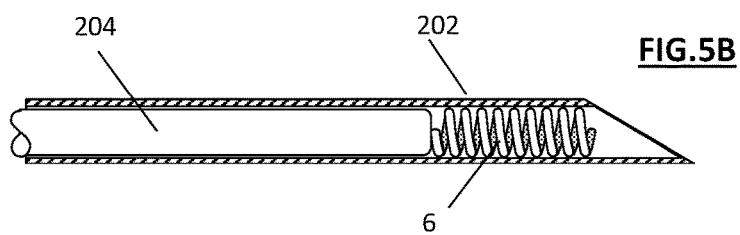

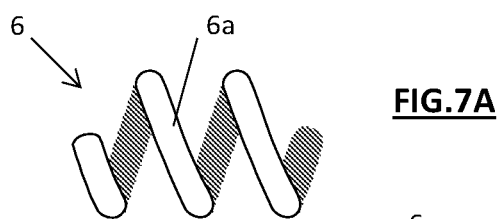
FIG.7A
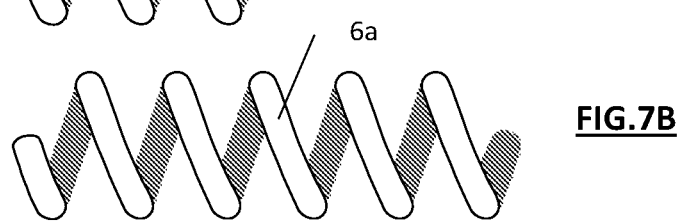
FIG.7B
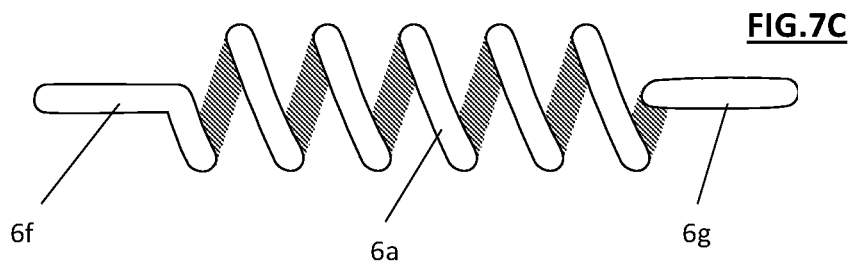
FIG.7C
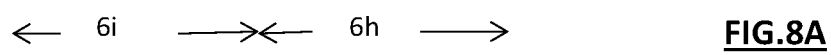
FIG.8A
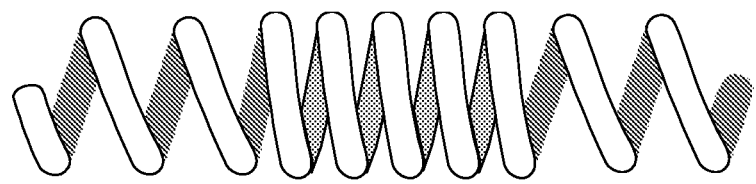
FIG.8B
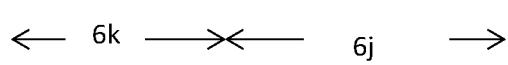

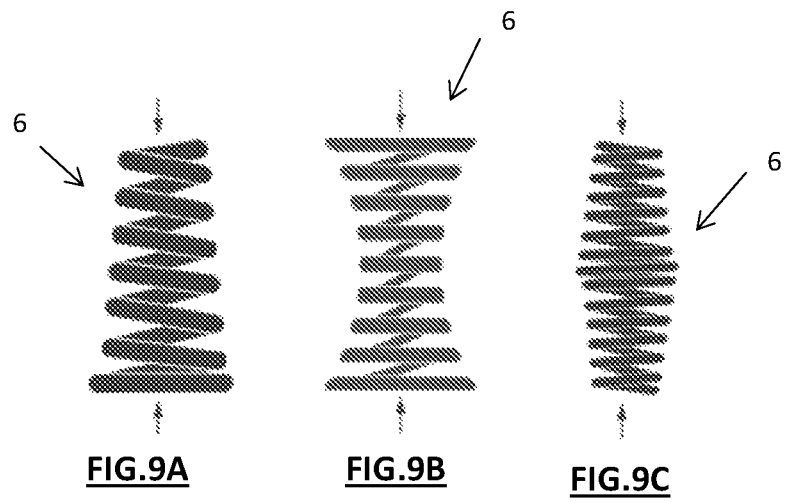
FIG.9A  FIG.9B  FIG.9C
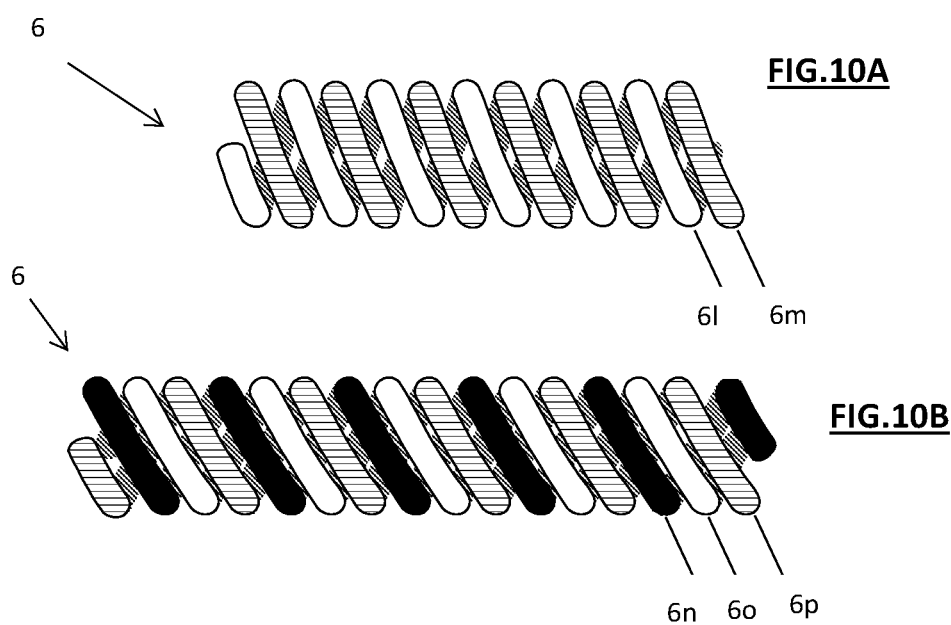
FIG.10A
FIG.10B

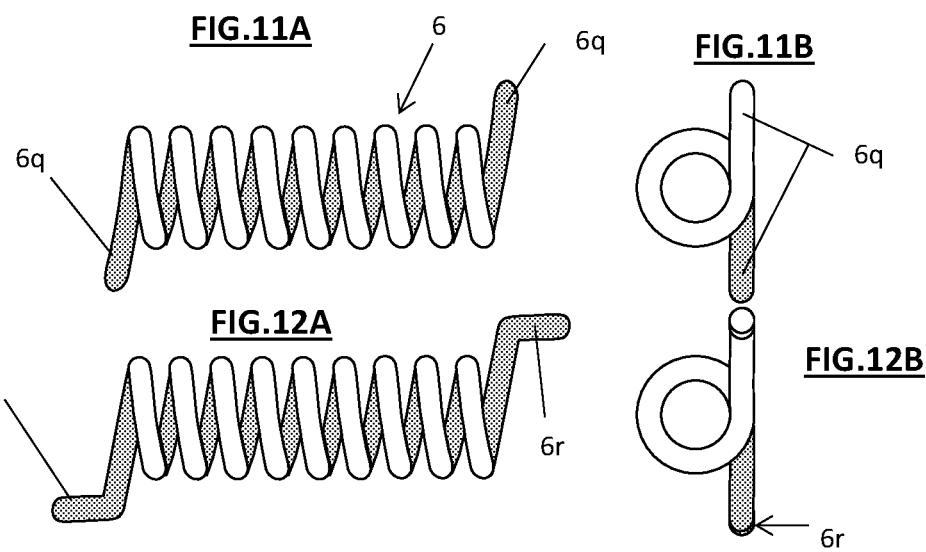
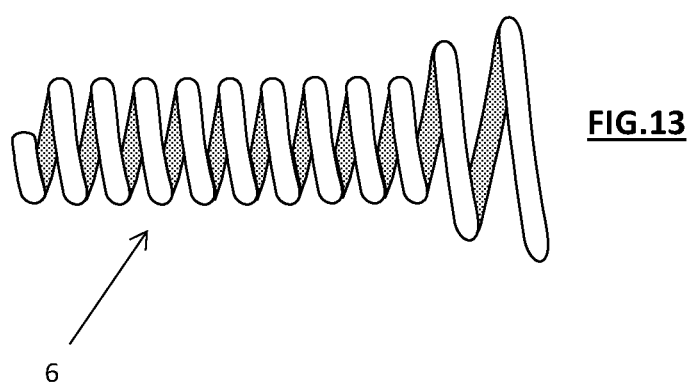
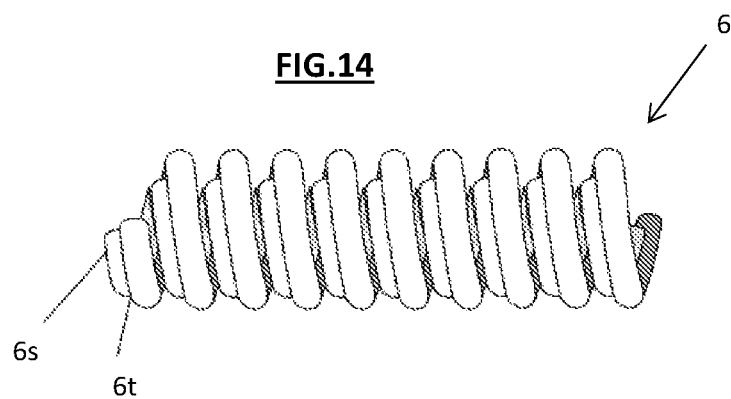

MAGNETIC MARKERS FOR SURGICAL GUIDANCE

CROSS REFERENCE TO RELATED APPLICATIONS

This is the national phase under 35 U.S.C. § 371 of International Application No. PCT/IB2019/052170, filed on Mar. 18, 2019, which claims priority to and the benefit of United Kingdom Patent Application No. 1804683.9 filed on Mar. 23, 2018, the entire disclosures of each of which are incorporated by reference herein.

FIELD OF THE INVENTION

This invention relates in general to the field of surgical guidance, more specifically to magnetic markers that aid in locating a lesion for surgical excision and to systems and methods for detecting such markers.

BACKGROUND OF THE INVENTION

Markers are used to guide surgeons to a region of interest during a surgical procedure, where the site of interest is not physically visible or palpable, for example a small tumour that needs to be excised. Ideally, such a marker will be deployable through a narrow gauge needle e.g. 18 g to 14 g in order to reduce trauma to the patient. Typically, such markers are less than 10 mm in length so as to be unobtrusive and to minimise trauma. The marker may be placed during a biopsy or other surgical procedure at a site of interest in the body, for example a cancer lesion. The marker is placed under imaging guidance such as ultrasound or X-ray/mammography. During subsequent surgery, the marker is detected and localised using a handheld probe which provides audible, visual or other feedback to the surgeon to guide the surgery. Typically the marker is excised along with the surrounding tissue.

One such approach is to use a marker containing a radioisotope such as Iodine 90 which can be detected using a handheld gamma detection probe. However, use of radioactive materials is closely regulated, making it challenging to set up a radioactive seed programme in all but the largest academic hospital centres.

US 2017/252124 (Cianna Medical) discloses a localization system which uses a combination of radio frequency (RF) and infra red (IR) radiation to detect a marker in the form of an implantable radar antenna. However, this system is limited by the low tissue penetration depth of IR radiation, the need for intimate tissue contact for good IR propagation, and the lack of robustness often associated with an implantable device containing antennae and electronic circuits.

US 2015/264891 (Health Beacons) discloses a further system based on radio frequency identification (RFID) tags that have been used as identity markers for pets and livestock. The drawback with this approach is that the small RFID tag constitutes a dipole antenna which has 'deadspots' when approached perpendicular to the dipole axis. This could cause confusion for surgeons using the system to localize a lesion. Miniaturizing the RFID tag sufficiently for convenient clinical implantation is also challenging.

A further approach is discussed in the Applicant's earlier published patent applications (for example, WO 2011/067576, WO 2014/032235 and WO 2014/140567) and uses magnetic fields and a magnetic marker with high magnetic susceptibility. A handheld probe generates an alternating field which excites a magnetically responsive marker, and detects the responding magnetic field. This approach is effective for deeper sensing and avoids the drawbacks of RF approaches. However, these systems will detect any magnetically responsive material in the vicinity of the probe, such as a ferromagnetic surgical tool or other metallic implanted device. This means that for effective operation they need to be used with non-ferromagnetic surgical instruments and away from other metallic implantables. Additionally, such a probe may respond to iron oxide nanoparticle suspensions used for sentinel node detection in breast cancer.

It has therefore proved problematic to provide a marker and detection system that possesses all the properties required for localising lesions, namely: a marker of a small size (<10 mm long); ability to deliver the marker through a small needle (eg. 16 g-18 g); ability to detect the marker using a handheld probe; and robust for implantation and surgical removal, together with a detection system that is able to distinguish the lesion marker from other magnetically responsive materials.

Sulla (Utilizing Magnetic Microwires For Sensing In Biological Applications, Jnl. of Elec. Eng., VOL 66. NO 7/s, 2015, 161-163) describes the use of glass coated amorphous microwires exhibiting large Barkhausen jump behaviour for medical applications, in particular as an implant that can be detected magnetically by applying an external field using the bistable behaviour of the microwire. In this respect, 'Large Barkhausen Jump' (LBJ) materials, undergo a rapid reversal of their magnetic polarization when excited by an external magnetic field whose field strength opposing the instantaneous magnetic polarization of the wire exceeds a predetermined threshold value. Thus, the material exhibits bistable behaviour, reversing between two magnetic polarisation states. Each reversal of magnetisation generates a magnetic pulse with harmonic components. The profile and number of harmonics is measured (out to many tens of harmonics) to identify the marker from other materials. Sulla concludes that a piece of wire 40 mm in length is required for functional sensing, but a marker of this length would be unsuitable for lesion localisation as many lesions are only a few millimetres in size.

These conditions suggest that this large Barkhausen jump behaviour described in the prior art is unsuitable for use as a lesion localisation marker for the following reasons:

The critical length required for the large Barkhausen jump of most such materials is greater than 5-10 mm making them too large for conveniently marking small lesions which may be only a few millimetres in size.

The switching field must be above a threshold $H_{sw}$ in order to drive the bistable behaviour, requiring large area excitation and large diameter sensing coils in the tens of centimetre range that generate large magnetic fields enabling the presence of a small wire to be detected from a useful range. However, for surgical guidance, a much more precise localisation of the marker is needed via a handheld or robotically guided detection probe. This limits the size of the detection coils to typically less than 20 mm diameter and thus limits the distance at which a marker can be detected. If the drive field is also generated in the probe, the detection ability decreases per the fourth or sixth order with distance from the probe. Thus while U.S. Pat. No. 4,660,025 discloses EAS markers excitable with switching fields of 0.6-4.5 Oe (0.06-0.45 mT), and U.S. Pat. No. 6,230,038 with a switching field of at least 1 Oe, the fields that can be generated at around 40 mm from a handheld probe are in the region of 0.5×10−3−

0.05 Oe (0.05-5 µT) when current, voltage, power and temperature range limitations are taken into account i.e. one to two orders of magnitude lower.

For some LBJ materials, the field at which the LBJ response is initiated increases with frequency, meaning that the wires become harder to excite at higher frequencies. For this reason, the prior art specifies frequencies below 3 kHz and preferably well below 1 kHz. This is undesirable for surgical guidance where in order to maximise signal to noise ratio from the very small fields being detected, it is desirable to average the signal over a number of cycles. Higher frequencies allow more averaging without the feedback response to the user appearing to have a lag or delay.

A further drawback of this type of system is the large anisotropy of the response from the marker wires, meaning that the response in the axial direction is much greater than the response in the transverse direction. In the EAS application, this does not present a problem because the system only needs to sense the presence of the marker, not its distance from the detector, and so large coils and high field strengths enable satisfactory EAS detection. However, in surgical guidance with a handheld probe, a response that varies depending on the direction of approach will be confusing to the user because the marker will appear to be a varying distance from the probe depending on the orientation of approach.

The Applicant's co-pending Application No GB1801224.5, the contents of which are incorporated herein by reference, describes an implantable magnetic marker comprising at least one piece of magnetic material that exhibits a large Barkhausen jump (LBJ) in its magnetisation curve, but where the marker is excited below the switching field required to initiate bistable switching behaviour of the LBJ material of the marker. The marker may also be below the critical length required to initiate bistable switching behaviour of the LBJ material. The concepts of 'critical length' and 'switching field' for LBJ wires are known from for example Vazquez (A soft magnetic wire for sensor applications, J. Phys. D: Appl. Phys. 29 (1996) 939-949). The marker in GB1801224.5 GB utilises a newly recognised "sub-bistable" mode of excitation for its LBJ material that causes a measurable harmonic response to be sensed even when the excitation field is below that of the 'switching field', traditionally considered necessary to initiate the classic bistable switching behaviour and a harmonic response.

Markers in the art all use straight pieces of LBJ wire. This is because the classic switching behaviour occurs through a cascade or domino effect in which the magnetic domains in the LBJ wires all flip at one time, and thus alignment of all the domains with the driving magnetic field is key. Domains not substantially aligned with the field will not flip or switch, meaning that the bistable behaviour of the magnetic response in which all the domains undergo a rapid reversal of magnetisation could not be realised thus resulting in the use of straight wires for detection. The use of any other configuration would be counter-intuitive based on the prior art literature.

However, when a straight piece of LBJ wire is excited, the magnetic response it gives is directional, that is there is a greater response along the axis of the wire and a much lower response in a direction perpendicular to the wire. For this reason, the inventors in co-pending Patent Application No. GB1801224.5, which uses their newly recognised "sub-bistable" mode of excitation for a marker comprising a LBJ material, describe how the dipole length of the LBJ material in the direction of the drive field is an important parameter for enabling harmonic response and detection. The inventors therefore teach providing a number of wires, for example in a tripod arrangement, such that the dipole length in any given direction is substantially similar. This enables a more uniform response to be achieved and provides one with the ability to measure the distance from the marker to a detection probe.

However, the provision of a satisfactory marker having the required uniform response with the same dipole length in each direction, does encounter a number a problems. In this respect, an implantable marker for locating a lesion is generally inserted through a small diameter deployment device requiring the marker to be able to reconfigure from <2 mm diameter to its final shape with the same dipole length in each direction. The tripod arrangement of the material or other 3D shape with similar dipole length in each direction results in a marker that has thin sections making it fragile or vulnerable to movement. If the marker fails to deploy correctly, then the response will be non-uniform and inaccurate.

Therefore, there is a need for a marker which is more robust and preferably does not need to make a reconfiguration on deployment.

The present invention aims to address this need.

SUMMARY OF THE INVENTION

According to a first aspect of the present invention there is provided a magnetic marker comprising:

at least one implantable marker, the implantable marker comprising at least one piece of magnetic material that exhibits a large Barkhausen jump (LBJ) in its magnetisation curve, wherein the LBJ material comprises at least one overlapping loop, said at least one loop being maintained during detection of the marker.

In a preferred embodiment, the marker comprises at least one piece of LBJ material having at least two full convolutions, preferably more, to form a coil or helix.

Surprisingly, the inventors have found that a coil of LBJ wire produces a measurable harmonic response in addition to a straight LBJ wire. At higher fields and larger diameter coils, this is a switching response similar qualitatively to the classic bistable switching described in the prior art. However, at lower fields and with smaller diameter coils, the response is 'sub-bistable' as described in the Applicant's co-pending Patent Application No. GB1801224.5.

Furthermore, while a single straight LBJ wire provides an axial response that is much greater than the transverse (perpendicular to the axis) response, more surprisingly the inventors have found that a coil of LBJ wire when excited in either the bistable or sub-bistable mode, has a larger transverse response than axial response, even when its length is several times its diameter.

The marker according to the invention may comprise a coil or helix of LBJ material having any number of complete turns or convolutions. The diameter and/or the pitch of the coils may be varied to adjust the response, including the ratio of the transverse to axial response in order to provide a more uniform response. For example, the marker may be formed of convolutions of an identical pitch or the convolutions may have a varying pitch along the longitudinal axis or length of the marker. Similarly, the marker may be formed of convolutions of an identical diameter or the convolutions may vary in diameter along the length of the marker, for example to provide a marker that is conical-shaped, barrel-shaped or hour glass shaped.

It is preferable to provide at least one axial member comprising at least one piece of LBJ material extending at least partially through the centre of the coiled marker to adjust the ratio of the transverse to axial response of the marker in order to provide a more uniform response. The at least one axial member may be in the form of a separate piece of material inserted through the coil or may be formed continuously with the coil at one or both ends of the marker.

The marker according to the invention may also comprise multiple coils. The multiple coils may be interwoven together or may comprise a coil having convolutions of a smaller diameter contained within a coil having convolutions of a larger diameter. The pitch may differ in the different coils but it is preferably similar to enable close meshing of multiple coils.

The marker may also be provided with at least one tissue engagement member to aid securement of the marker to tissue at a lesion site. For example, one or both ends of the coiled marker may be provided with a hook or prong, preferably being formed integrally with the marker.

Preferably, the marker comprises less than 5 mg of LBJ material. The material may be provided in the form of a wire that is wound into a coil of the required pitch and diameter. Examples of such materials include, but are not limited to, iron-, cobalt- and nickel-rich glass-coated amorphous microwires, iron-silicon-boron based amorphous microwires, iron-cobalt based amorphous microwires, and/or bulk metallic glass wires.

Preferably, the marker is deployable from a needle having an inner diameter of less than 2 mm. More preferably, the aspect ratio of the marker prior to deployment is >3. It is preferable for the coiled marker to be deployable in its final form without the need for a shape transition, thereby reducing the likelihood of the marker failing to deploy correctly which may affect the accuracy and uniformity of any detected response from the marker.

The wires may be coated or provided within a housing. Preferably, the LBJ wire is coated or provided within a tube of non-magnetic material to provide composite properties such as strength, stiffness, flexibility and biocompatibility. For example, the wire may be coated with a polymer coating such as FEP, Parylene, PTFE, ETFE, PE, PET, PVC, or silicone or an epoxy-based encapsulant. Alternatively, the wire may be encased in a tube prior to being formed into the required coiled marker shape. Suitable materials for the tube include Nitinol, titanium, stainless steels and other biocompatible alloys. Preferably the material is non-magnetic and has a relatively low conductivity. More preferably, the housing is formed from a material having a resistivity greater than $2 \times 10^{-7}$ $\Omega$m. The resistivity may also be increased through selective cutting of the tube such as with an interrupted laser cut spiral. This may also aid in winding of the tube.

The tube, especially if selectively cut, may be further coated or housed within a biocompatible sheath prior to coiling and/or the coiled marker may be housed or coated in a similar sheath. Preferably this sheath is also an insulating layer.

The marker housing may be formed from a moulded or extruded material. For example, a polymer may be extruded around the magnetic wire to form a coated wire that can then be formed into a loop. Suitable materials for the coating or overmoulding include PEEK, PEKK, polyethylene, polypropylene, polyester, polyurethane, polyimide, polyether block amide, polyamide, PTFE, FEP and silicones.

In one embodiment, a marker according to the present invention includes a housing comprising one or more strands of material which are wound around the magnetic material, for example in the form of a helix, to form a more robust construction prior to forming into the final marker shape. Preferably the surrounding material completely encloses the magnetic marker material. The strands of the surrounding material could be formed from one material or from more than one type of material to obtain a different profile of material properties such as strength, stiffness, resistivity, or echogenicity. The surrounding material could be wound in a single layer or in multiple layers within the scope of the invention. Similarly, the layers could be wound in alternate senses or directions, and could comprise different materials or cross sections and may be further coated or housed within a biocompatible sheath prior to coiling and/or the coiled marker may be housed or coated in a similar sheath.

Thus, the marker is formed of a coil that can be deployed from a needle in its final form without the need for a shape transition. However, in an alternative embodiment, the marker can comprise a resiliently deformable tube containing the LBJ wire such that the coil expands on deployment to a larger size.

It is to be appreciated that the cross section of the marker is not limited to a particular shape. For example, the marker may be round, rectangular or triangular in cross-section. It may be preferable to provide a marker having a section in which there is a substantially straight side, for example rectangular or triangular in order to provide angles at which there is an increased magnetic response relative to other angles, e.g. when a straight section is aligned with the excitation field.

The marker for use in the present invention is preferably configured such that when implanted into the body the magnitude of a harmonic response from the marker when interrogated by an alternating magnetic field is substantially the same when measured from any direction relative to the marker, and allows the distance between the probe and the marker to be determined.

According to a second aspect of the present invention, there is provided a detection system for locating a marker, the system comprising:

a magnetic marker according to the first aspect of the present invention;

at least one drive coil arranged to excite the marker with an alternating magnetic field and at least one sense coil arranged to detect a signal received from the excited marker;

a magnetic field generator arranged to drive an alternating magnetic field through the at least one drive coil; and at least one detector arranged to receive the signal from the sense coil and detect one or more harmonics of the drive frequency in the received signal.

Depending upon the size and configuration of the marker, the drive coil may excite the marker above a threshold that initiates bistable switching behaviour of the LBJ material. Alternatively, and more preferably, the at least one drive coil excites the marker below the switching field required to initiate bistable switching behaviour of the LBJ material of the marker.

Preferably, a harmonic response is used to determine location/distance/proximity of the marker from a probe. More preferably, the ratio of maximum to minimum harmonic response with direction is <3.

In a preferred embodiment of this aspect of the invention, both the drive and sense coils are provided in a handheld probe. Alternatively, only the sense coil may be provided in a handheld probe. In this embodiment, a larger drive coil may be provided external to the probe to enable an increased magnetic field to be generated at the marker site. For example, the drive coil may be provided within a pad for placement near or beneath a patient.

The detection system preferably comprises an output module for processing the received harmonic signal and providing at least one indicator to the user relating to a location of the marker relative to the sense coil, for example an indication of the proximity, distance, direction and/or orientation of the marker with respect to the sense coil.

More preferably, the system processes one or more aspects of the harmonic response of the marker, such as the magnitude of one or more odd harmonics (e.g. $3^{rd}$ and $5^{th}$), even harmonics (e.g. $2^{nd}$, $4^{th}$ and $6^{th}$) or a combination of both or the ratios of these harmonics to each other or to the fundamental frequency. Appropriate filters may be provided to enhance the drive and sensed signals.

The output module may include a visual display or sound generator.

According to a third aspect of the present invention there is provided a method of detecting an implantable marker, the implantable marker comprising at least one piece of magnetic material that exhibits a large Barkhausen jump (LBJ) in its magnetisation curve, wherein the LBJ material comprises at least one overlapping loop maintained in the marker during detection thereof, the method comprising applying an alternating magnetic field to the marker to excite the marker to initiate bistable or sub-bistable switching behaviour of the LBJ material of the marker; and detecting one or more harmonics of the drive frequency of a signal received from the excited marker caused by a change in magnetization of the marker.

Preferably, the marker is excited below the switching field required to initiate bistable switching, wherein the application of the alternating magnetic field to excite the marker below the switching field results in a sub-bistable response being detected for the marker.

Preferably, the drive frequency is above 1 kHz, preferably being in the range 1-100 kHz, especially 10-40 kHz.

The method preferably includes measuring an aspect of the harmonic response of the marker to provide an output relating to the location of the marker. For example, this may be the amplitude of one or more odd harmonics, even harmonics or a combination of both, the ratios of these harmonics to each other or to the fundamental frequency. Appropriate filtering and processing of the signals may be provided to enhance the output provided by the method.

BRIEF DESCRIPTION OF THE DRAWINGS

For a better understanding of the present invention and to show more clearly how it may be carried into effect, reference will now be made by way of example only, to the accompanying drawings, in which:

FIG. 4 is a block diagram of a magnetic detection system for use with a marker of the present invention;

FIGS. 5A and 5B illustrate a deployment device for deployment of a marker according to the present invention;

FIGS. 7A to 7C illustrate further embodiments of a marker according to the present invention;

FIGS. 8A and 8B illustrate alternative embodiments of a marker according to the present invention, the markers each having a variable pitch.

FIGS. 9A to 9C illustrate yet further embodiments of a marker according to the present invention, wherein the markers have convolutions of varying diameter along the length of the coil;

FIGS. 10A and 10B illustrate yet still further embodiments of a marker according to the present invention, wherein the markers include multiple intermeshed coils;

FIGS. 11A and 12A are side views and FIGS. 11B and 12B are end-on views of a marker according to alternative embodiments of the present invention;

FIG. 13 illustrates yet another embodiment of a marker according to the present invention;

FIG. 14 illustrates still yet a further embodiment of a marker according to the present invention;

DETAILED DESCRIPTION OF THE INVENTION

The present invention relates to a magnetic marker that can be implanted for marking a site in the body, for example the site of a lesion and subsequently be detected and localised using a handheld probe. The invention also describes a detection system and method for locating the position of the implanted marker in the body.

Figure 1A:
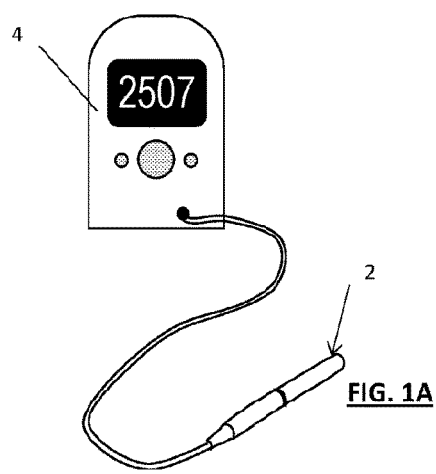
FIG. 1A is a schematic diagram of a detection system for use with a marker according to the invention, the detection system forming part of the prior art.
Figure 1B:
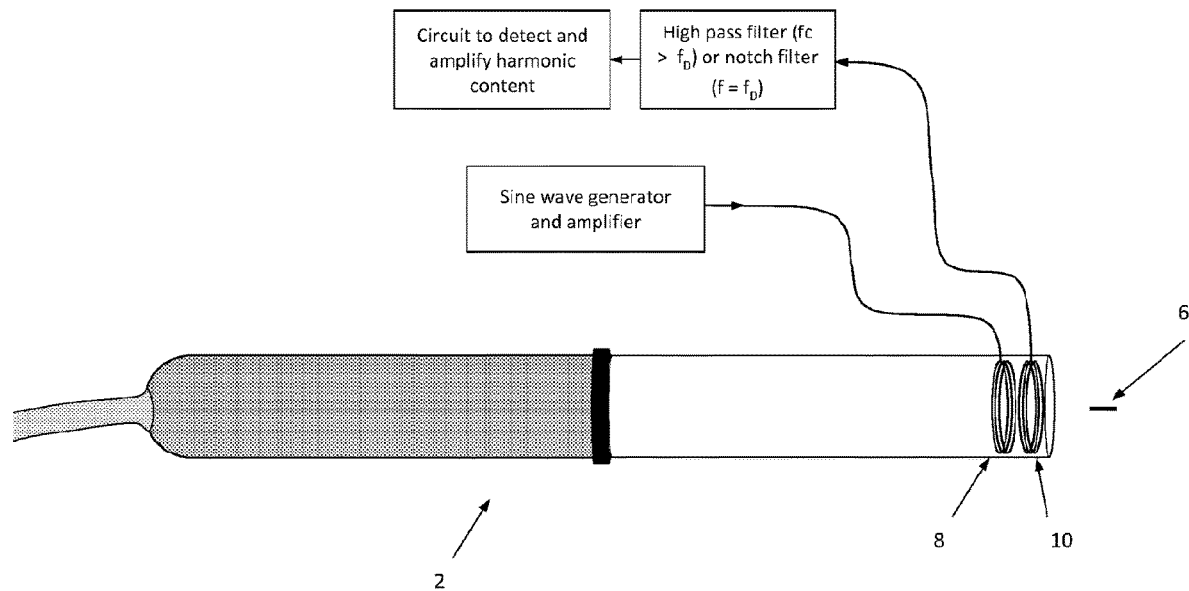
FIG. 1B illustrates the components of the detection system shown in FIG. 1A in further detail.

FIGS. 1A and 1B of the accompanying drawings show schematic diagrams of an example of a detection system according to the prior art that may be used to detect a marker according to the present invention. The detection system comprises a probe 2 connected to a base unit 4. The probe has one or more drive coils 8 (see FIG. 1B) that generate an alternating magnetic field to excite a magnetic marker 6. The probe 2 of the detection system further contains one or more sense coils 10 arranged to detect the changes in the magnetic field caused by the change in magnetisation of the marker.

Figure 2:
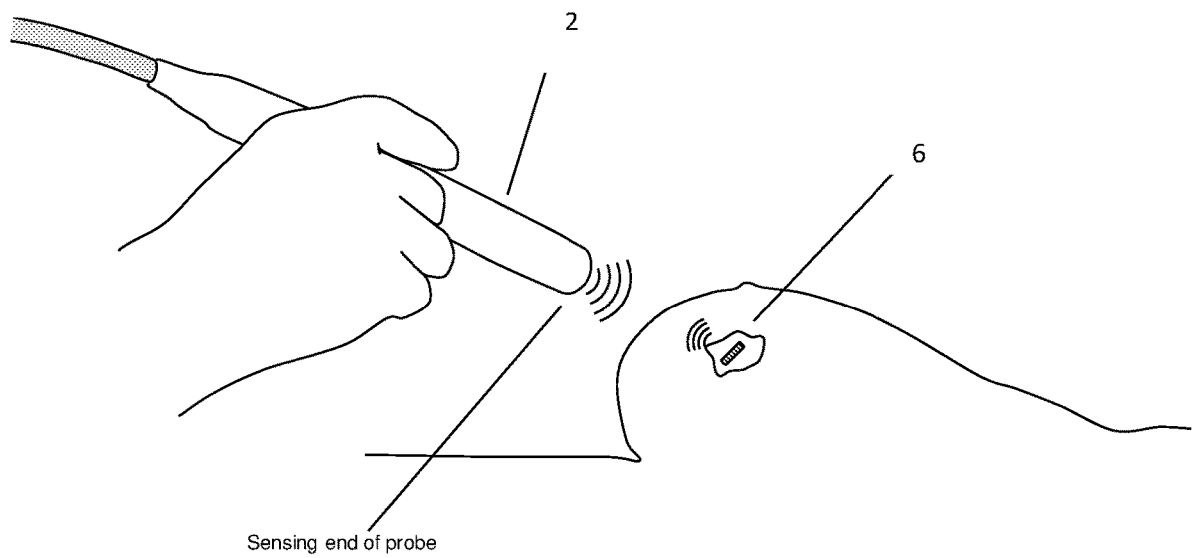
FIG. 2 illustrates use of a detection system to locate an implanted marker.

FIG. 2 illustrates how the marker 6 may be implanted into a patient's breast and then located using the probe 2.

It is desirable to provide improved markers for enhanced localisation by the probe. The Applicant's co-pending Application No. GB1801224.5 describes one such marker. The marker comprises at least one piece of magnetic marker material having a large Barkhausen discontinuity in its magnetisation curve, also known as a large Barkhausen jump material (or a LBJ material). When the LBJ material is exposed to an external magnetic field whose field strength opposing the instantaneous magnetic polarization of said length of material exceeds a predetermined threshold value, the switching field $H_{SW}$, its magnetic polarization undergoes a rapid reversal. This reversal of magnetisation generates a magnetic pulse with rich harmonic components. Conventionally, the markers are sized to be above the so-called 'critical length', that is the length at which the magnetization can undergo the full bistable transition or 'flipping' behaviour which is required to generate a significant harmonic response. However, the inventors found that a harmonic response can be obtained from markers significantly below their critical length and/or below the switching field $H_{SW}$ in a newly recognized "sub-bistable" mode and that this is advantageous for use for localization of the implantable marker.

Figure 3A:
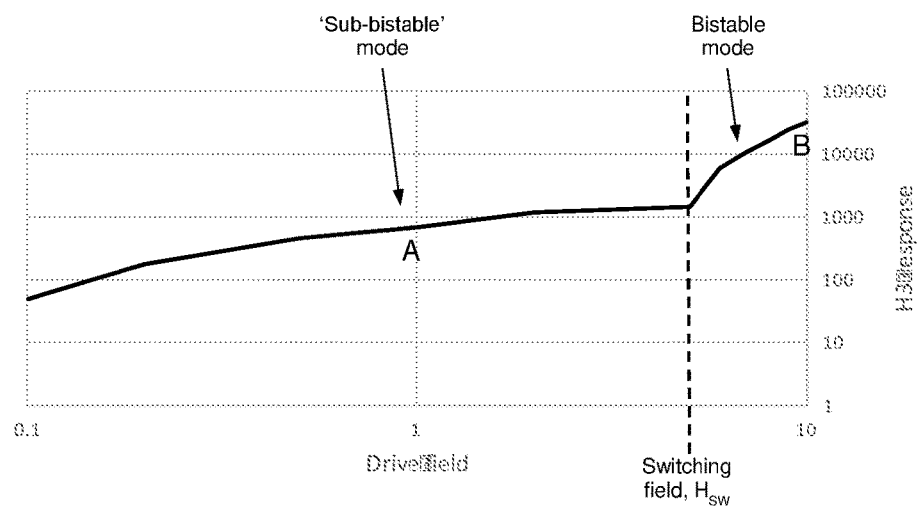
FIGS. 3A and 3B illustrate a third harmonic (H3) response (arbitrary units) from an LBJ wire as the magnitude of the 100 Hz excitation field is increased, shown with both log-log and log-linear scales respectively.
Figure 3B:
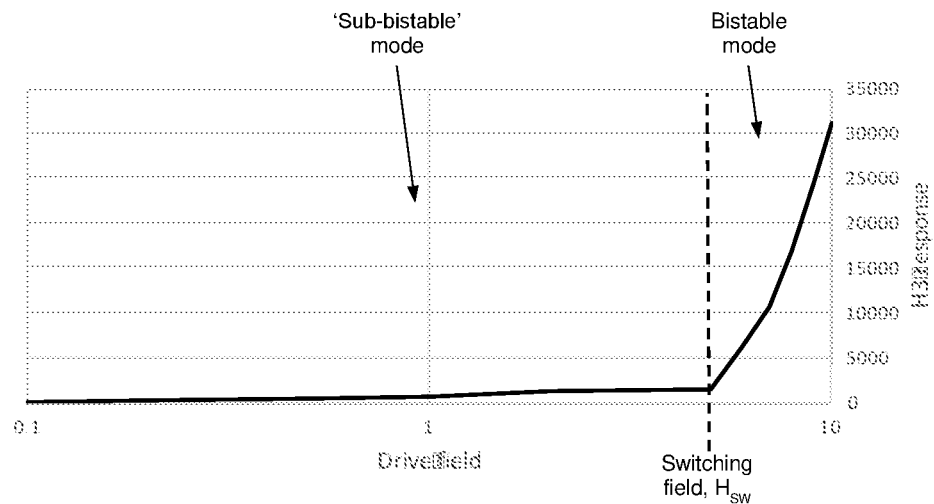

FIGS. 3A to 3E illustrate this bistable and so-called "sub-bistable" behaviour of the LBJ material which may be incorporated into an implantable marker. FIGS. 3A and 3B illustrate a third harmonic (H3) response (arbitrary units) from an LBJ wire as the magnitude of the 100 Hz excitation field is increased, shown with both log-log and log-linear scales respectively. As demonstrated, when a piece of cobalt-iron amorphous LBJ microwire above the critical length is excited with an alternating magnetic field at 100 Hz, the third harmonic (H3) response is shown in FIG. 3A. H3 is here taken as representative of the harmonic content of the marker response. Once an H3 response is distinguishable from noise, it increases in an approximately linear relationship with excitation field. This continues until the switching field is reached, at which point the response increases dramatically in magnitude as the bistable switching is initiated (region B in FIG. 3A). It is this point at which LBJ above a critical length is normally identifiable. The log-linear and log-log scales clearly illustrates the change in mode. However, FIG. 3A shows that by using the "sub-bistable" mode (region A in FIG. 3A), the marker can be detected even when the field is almost 2 orders of magnitude lower than the switching field required for bistable behaviour. This means that for a given drive field, the marker can be detected at a much greater distance from the probe.

Figure 3C:
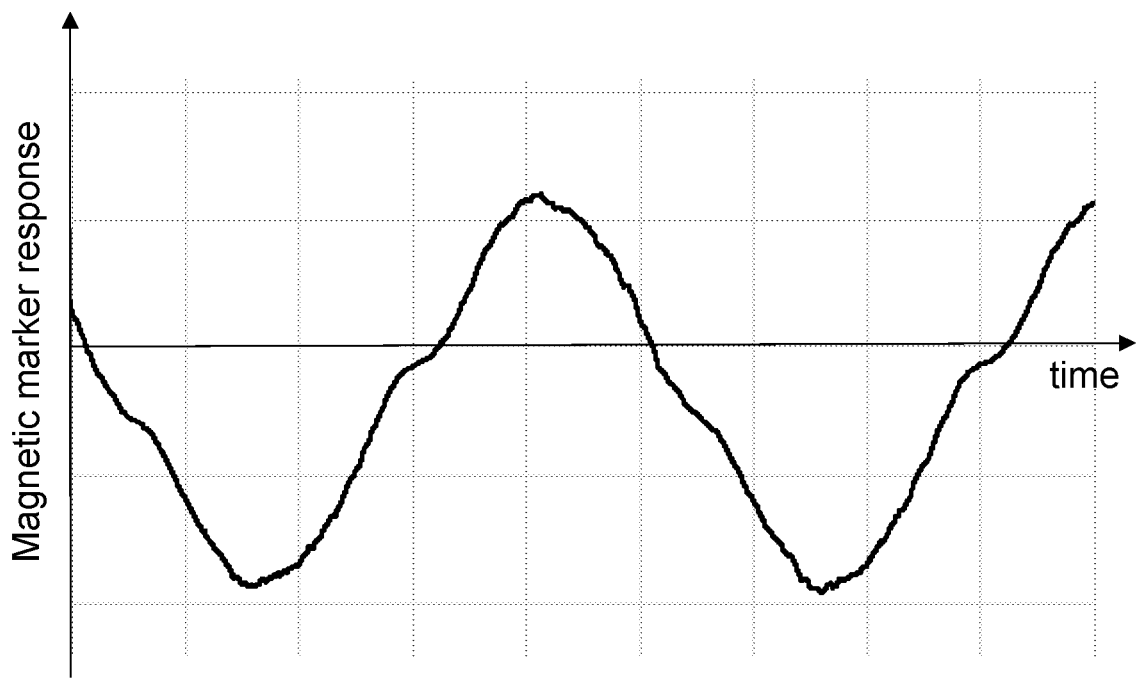
FIG. 3C shows the time-domain response in the sub-bistable region at point A in the top graph of FIG. 3A when driven by a sinusoidal wave.
Figure 3D:
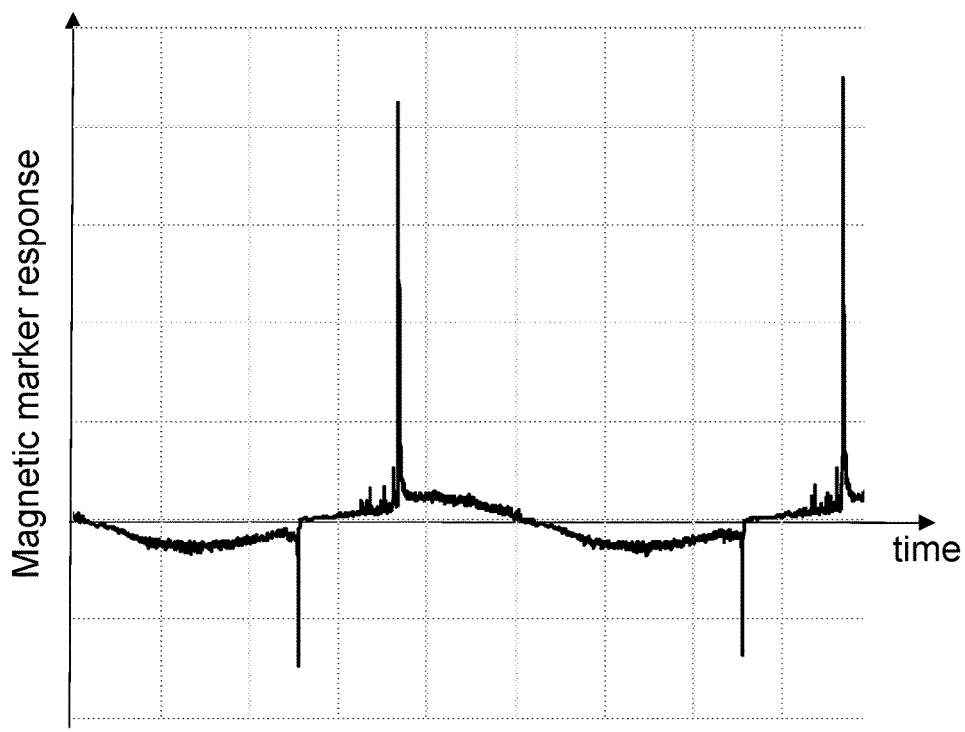
FIG. 3D shows the time-domain response in the bistable region at point B in the graph of FIG. 3A when driven by a sinusoidal wave.
Figure 3E:
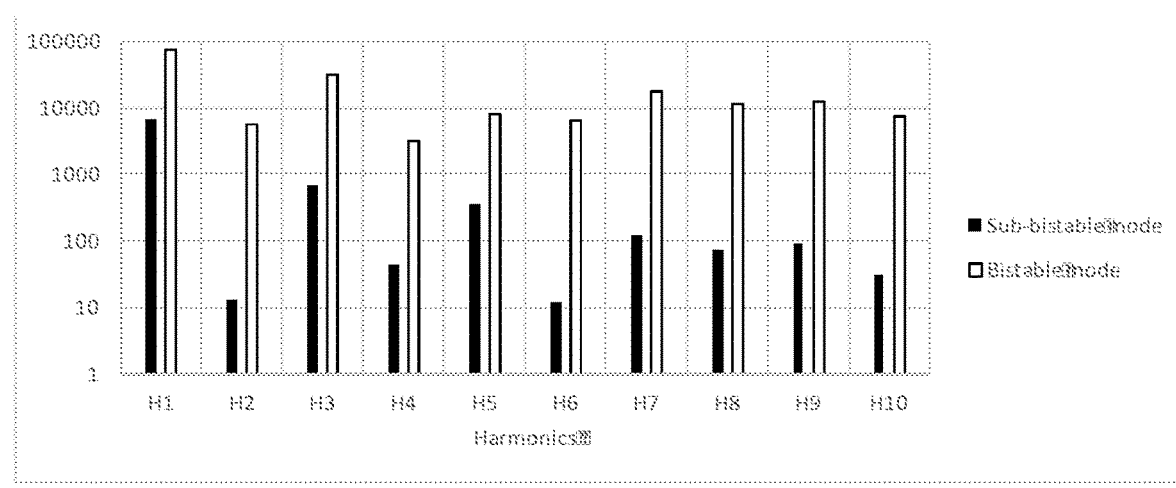
FIG. 3E is the Frequency domain response from an LBJ wire in the sub-bistable and bistable switching modes at 100 Hz excitation frequency.

FIG. 3C shows the time-domain response in the sub-bistable region when driven by a sinusoidal wave. It is seen as a distorted sine wave, in contrast to the bistable time-domain response which shows the classic short pulses as the magnetisation reverses (see FIG. 3D). In the frequency domain, the rich harmonics of the bistable mode contrast with the less rich harmonic response of the sub-bistable mode (see FIG. 3E). However, such harmonic response is still richer than the response from non-bistable amorphous wires and thus this response may be used to accurately identify a marker even when the length of wire is below the 'critical length' and the excitation field is below the 'switching field'.

FIG. 4 of the accompanying drawings shows a block diagram of a magnetic detection system which may be used to locate a marker according to the prior art or according to the invention. A frequency generator 12 for example an oscillator or waveform generator ($f_D$ is 100 Hz to 50 kHz) generates a preferably sinusoidal alternating signal which excites one or more drive coils 8. The one or more drive coils generate an alternating magnetic field that extends into the tissue containing a magnetic marker 6 comprising at least one piece of a large Barkhausen jump material (LBJ).

The alternating magnetic field excites the marker 6 and the magnetisation of the marker leads to the generation of harmonic components in the field. Depending on the arrangement of the marker, the harmonics may be odd harmonics, ($3^{rd}$, $5^{th}$, $7^{th}$ etc.) or even harmonics ($2^{nd}$, $4^{th}$, $6^{th}$ etc.) or a combination of both odd and even harmonics. The marker is detected by measuring the magnitude of one or more of the harmonic frequencies directly or by measuring the ratio of the magnitude of one or more harmonics to others or to the magnitude of the fundamental frequency.

The response from the marker is detected by one of more sense coils 10 to generate a sense voltage or current. The sense coils may be in a handheld or robotic probe. A high-pass or notch filter 14 may be arranged to filter out or attenuate at least components of the sense signal at the drive frequency so that the resulting signal has minimal content at the drive frequency and comprises higher harmonic components of the signal, for example the second, third, fourth, fifth or seventh order harmonics or combinations of these. The filter may take the form of a passive LCR type filter comprising a known arrangement of for example capacitors, inductors and resistors or an active filter comprising a known arrangement for example based on one or more op-amps.

The filtered signal may be fed to a harmonic detection circuit 16 which amplifies one or more harmonic components of the signal and converts the signal 18 to a measure of distance from the probe to the marker. A user display and sound generator 20 provides a visual and audio output to the user indicating for example, the proximity of the marker or the magnitude of the magnetic signal. The system may indicate the proximity, size, distance to, direction or orientation of the marker, or combinations of these.

When a straight piece of LBJ wire is excited, the magnetic response it gives is directional, that is there is a greater response along the axis of the wire and a much lower response in a direction perpendicular to the wire. For this reason, the inventors co-pending Application GB1801224.5 describes how the dipole length of the LBJ material in the direction of the drive field is an important parameter for enabling harmonic response and detection and discloses the use of a number of wires, for example in a tripod arrangement, such that the dipole length in any given direction is substantially similar. However, such markers have thin sections making them fragile or vulnerable to movement. This can make satisfactory deployment of the marker difficult.

FIGS. 5A and 5B show an example of a deployment system according to the prior art that may be used to deliver a marker to a surgical site. FIG. 5A shows a deployment device 200 comprising a needle 202 and a plunger 204. In use, the needle is inserted into the target tissue under imaging guidance. The deployment device is arranged such that on depression of the plunger, the magnetic marker is deployed from the end of the needle into the target tissue. FIG. 5B shows a detail of the distal end of the deployment device 200 containing a magnetic marker 6 in the needle 202 together with a plunger 204.

It is critical that the marker 6 deploys correctly from the needle because otherwise the similarity or identity of the dipole length in each direction will be affected, leading to a non-uniform and inaccurate response.

The present invention provides improved markers that contain LBJ material which may be detected using their conventional bistable behaviour or using the recently identified "sub-bistable" mode. The inventors have surprisingly found that markers that have a LBJ material formed into a coil or loop produce a measurable harmonic response. This was not to be expected because classic switching behaviour occurs through a cascade or domino effect in which the magnetic domains in the LBJ wires all flip at one time, and thus alignment of all the domains with the driving magnetic field is key. Domains not substantially aligned with the field will not flip or switch, thus resulting in the use of straight wires for detection. Thus, the skilled person would consider the use of any other configuration to be counter-intuitive based on the prior art literature. The coiled markers according to the invention demonstrate switching response similar qualitatively to the classic bistable switching described in the prior art at higher fields and larger diameter coils, while at lower fields and with smaller diameter coils, the response is 'sub-bistable' as described in GB1801224.5.

Furthermore, while a single straight LBJ wire provides an axial response that is much greater than the transverse (perpendicular to the axis) response, more surprisingly, the inventors have found that a coil of LBJ wire when excited in the sub-bistable mode (and indeed the bistable mode), has a larger transverse response than axial response, even when its length is several times its diameter.

Figure 6A:
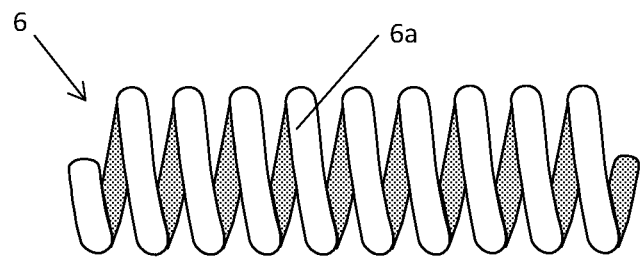
FIGS. 6A to 6D illustrate embodiments of a marker according to the present invention.
Figure 6B:
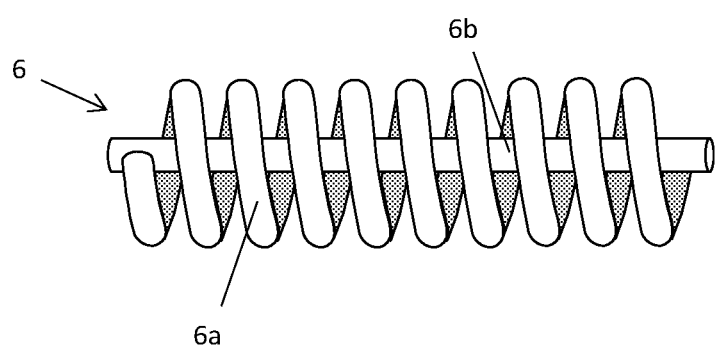
Figure 6C:
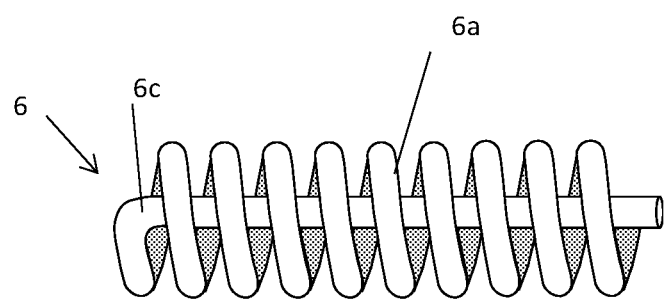
Figure 6D:
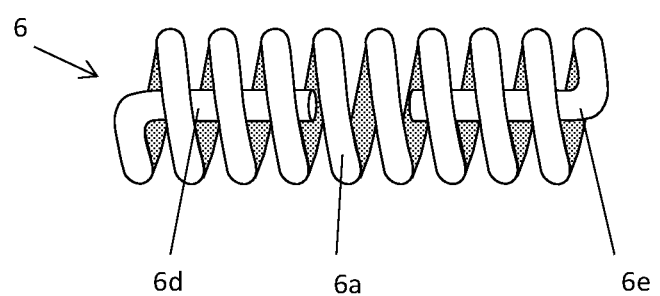

FIGS. 6A to 6D illustrate different embodiments of a marker 6 according to the invention. Each marker 6 comprises a coil 6a of magnetic material. FIG. 6A shows a simple coil of magnetic marker material. FIG. 6B shows a coil 6a with a further piece of magnetic material, for example in the form of a rod of wire 6b placed axially inside the coil. FIG. 6C shows a coil 6a with one end of the coil folded back into the centre of the coil to form an axial element 6c inside the coil. FIG. 6D shows a further embodiment in which both ends of the coil 6a are folded back through and towards the centre of the coil to form axial elements 6d, 6e inside the coil. These axial elements inside the coil increase the magnitude of the axial magnetic response which can be used to obtain the desired uniformity or asymmetry of response.

FIGS. 7A to 7C shows coiled markers according to the present invention, with a different pitch of the coil 6a compared to the tight pitch shown in FIGS. 6A to 6D. FIG. 7C shows a coiled marker 6 in which the ends 6f, 6g continue axially outside the coil. The extended ends increase the magnitude of the axial magnetic response which can be used to obtain the desired uniformity or asymmetry of response.

FIGS. 8A and 8B show embodiments of a coiled marker according to the present invention in which the pitch of the coil varies through its length. FIG. 8A shows a coil with a central region 6h with a smaller pitch and outer regions 6i with a larger pitch. In contrast, FIG. 8B shows a coiled marker having a central region 6j with a larger pitch and outer regions 6k with a smaller pitch. It is to be appreciated that the pitch can be varied in any way along the length of the marker in discrete or continuous ways within the scope of the invention. As can be seen from the values in Table 1 below, an increase in the pitch causes the magnitude of the axial magnetic response to increase relative to the transverse response. This can also be used to obtain the desired uniformity or asymmetry of response.

FIGS. 9A to 9C illustrate alternative embodiments of a marker according to the invention wherein the diameter of the marker varies along the length of the marker. For example, FIG. 9A reduces the diameter of the convolutions of the coil from one end of the coil to another to form a conical shaped marker. FIG. 9B reduces the diameter of the convolutions of the coil from both ends of the coil towards the centre to form a hourglass shaped marker. FIG. 9C increases the diameter of the convolutions of the coil from both ends of the coil towards the centre to form a barrel shaped marker. Varying the diameter of the convolutions of the coiled marker along its length is advantageous to modify the magnetic response from different directions. Coiled makers having both different diameters and pitches fall within the scope of the invention. Increasing the number of coils and their diameter increases the magnitude of the response in a cumulative fashion, although there are some losses due to the proximity of the coils to each other. Thus these arrangements could be used to modify the uniformity of the magnetic response as desired.

Further embodiments of a marker according to the present invention are shown in FIGS. 10A and 10B, wherein the marker is provided with multiple coils combined or intermeshed within the marker. FIG. 10a illustrates a marker with two coils 6l, 6m and FIG. 10B shows a marker with three coils 6n, 6o, 6p. Each of the coils that are combined could have a different diameter and/or pitch within the scope of the invention. However, it is preferable for the multiple coils to have similar diameters and pitches such that they can mesh closely together as shown in FIGS. 10A and 10B to maximise the efficient use of space within the marker envelope. Additional coils increase the magnitude of the response in an approximately additive fashion, although there are some losses due to the proximity of the coils to each other.

FIGS. 11A to 13 illustrate further embodiments of the marker in which additional features are present to aid engagement with tissue once the marker has been implanted into a patient. Examples include a hook or prong or conical coil shapes, and be at one or both ends of the marker, or protrude from the side of the marker. For example, FIGS. 11A and 11B show a coiled marker wherein the ends of the coil extend away from the coil 6 to provide engagement members 6q. FIGS. 12A to 12B has these ends shaped to form a hook-like engagement feature 6r. The features may be formed from the same material as the coil or from a different material. The features may further be arranged to compress within the marker deployment device and then, resiliently or via a shape memory change, transform into their final shape upon deployment. Such features may be adapted to aid engagement with a particular kind of tissue. For example a larger diameter coil or conical coil shape, such as that shown in FIG. 13, may be beneficial for locating in a lumen, blood vessel, or airway in the lung. Barb shaped features may be beneficial for locating in breast tissue or a biopsy cavity.

FIG. 14 shows yet another embodiment of a marker according to the invention in which a smaller coil 6s is combined with a larger outer diameter coil 6t within the marker. This is advantageous in order to provide more magnetic material within the same space envelope defined by a narrow gauge delivery needle. Again, the coils could be different diameters and pitches within the scope of the invention but preferably are closely wound with minimal space between each turn in the coil in order to maximise the efficient use of space within the marker envelope.

Figure 15A:
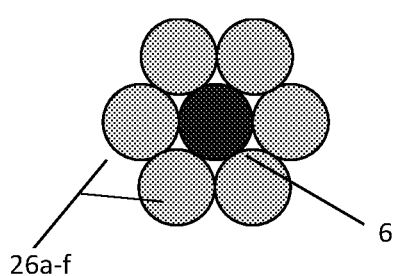
FIGS. 15A and 15B illustrate another embodiment of a marker according to the invention wherein the magnetic material is part of a stranded wire or braid.
Figure 15B:
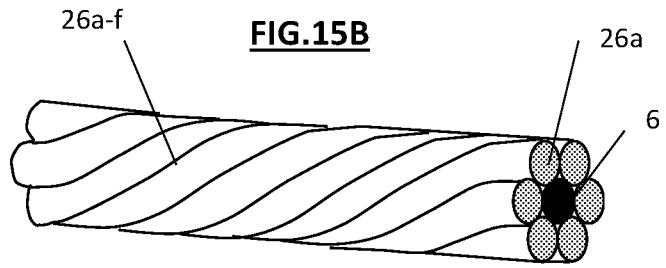
Figure 16A:
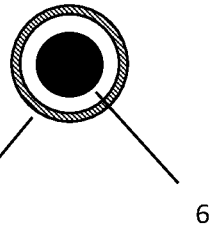
FIGS. 16A and 16B illustrate yet another embodiment of a marker according to the invention wherein the magnetic material is within a tubular housing.
Figure 16B:
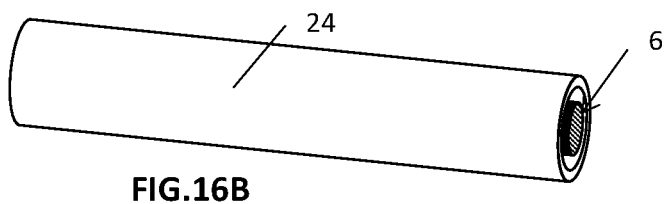
Figure 17A:
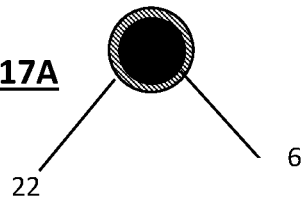
FIGS. 17A and 17B illustrate yet still a further embodiment of a marker according to the invention wherein the magnetic material is provided with a coating.
Figure 17B:
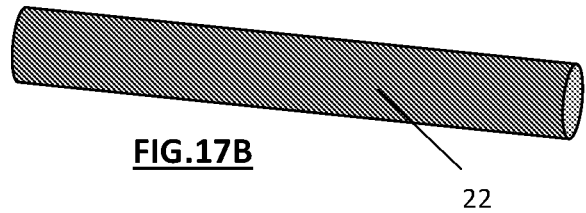

The LBJ magnetic material that is wound into coil as herein described may be combined with other materials to improve the marker. For example, the marker may be packaged within other materials. In this respect, markers for implantation need to be both biocompatible to prevent a reaction with body tissue, and robust. Some preferred magnetic materials are thin (wires below 0.15 mm in diameter), and contain non-biocompatible materials. Therefore, to improve the biocompatibility and robustness of the marker, it is preferable to provide a housing or coating for the magnetic material. FIGS. 15A to 18B of the accompanying drawings illustrate alternative combinations of the magnetic material with other materials to form the packaged marker. This may be in the form of a coating 22, as shown in FIGS. 17A to 17B. For example, the magnetic wire may be coated with a polymer coating such as FEP, Parylene, PTFE, ETFE, PE, PET, PVC or silicone, or an epoxy-based encapsulant. Alternatively or additionally, the magnetic material may be encased in a tube 24 prior to being formed into the required marker shape, as shown in FIGS. 16A and 16B (shown in the pre-formed condition). This arrangement improves the robustness of the magnetic material. Suitable materials for the tube include Nitinol, titanium, stainless steels and other biocompatible alloys. Preferably the material is non-magnetic and has a relatively low conductivity, in order not to influence the magnetic response of the marker. Preferably the volume resistivity is greater than $2 \times 10^{-7}$ Ωm (Ohm-metres) in order to minimise the production of Eddy currents within the housing which could affect the magnetic response.

In a preferred embodiment a biocompatible and insulating coating or sheath such as FEP, Parylene, PTFE, ETFE, PE, PET, PVC or silicone further surrounds the tube 24. This insulating layer stops conduction between the turns within the coils further reducing the effects of Eddy current on the magnetic response of the marker.

Table 2 below shows the influence of the conductivity of the tube material on the harmonic response for straight lengths of an LJB wire in different tube materials. The signal from the LBJ wire in the copper tube with a material resistivity of $0.17 \times 10^{-7}$ Ωm is at least 16 times lower than the signal from similar wires in tubes made with other materials with a higher resistivity of greater than $2 \times 10^{-7}$ Ωm. The use of selective cutting of the tube such as with an interrupted laser cut spiral, which also supplies flexibility for coiling, may also be used to increase resistance and reduce the production of Eddy currents. The polymer coating may be applied before or after the material or tube is formed into a coil.

In a preferred embodiment, the marker housing could be formed from a moulded or extruded material. For example, a polymer may be extruded around the magnetic wire to form a coated wire that can then be formed into a loop or coil. Any of the embodiments above could also be over-moulded with a polymer to form a marker. The advantage of such an embodiment is that the polymer could provide biocompatibility and also make the manufacturing process simpler and less costly. The use of polymers also minimises any Eddy current effects seen with metal coatings or housings that could affect the magnetic response. Suitable materials for the coating or overmoulding include PEEK, PEKK, polyethylene, polypropylene, polyester, polyurethane, polyimide, polyether block amide, polyamide, PTFE, FEP, PET and silicones.

In another preferred embodiment, a marker according to the present invention includes a housing comprising one or more strands of material 26 which are wound around the magnetic material to form a more robust construction prior to forming into the final marker shape. FIGS. 15A and 15B show, for example, a piece of marker material 6 with 6 strands of a different material 26a-f wound around it in a helical arrangement (see FIG. 15B). The surrounding material could be in the form of wires with round, rectangular or other cross section. Preferably the surrounding material completely encloses the magnetic marker material. The strands of the surrounding material could be formed from one material or from more than one type of material to obtain a different profile of material properties such as strength, stiffness, resistivity, magnetic response, radiopacity or echogenicity. The surrounding material could be wound in a single layer or in multiple layers within the scope of the invention. Similarly, the layers could be wound in alternate senses or directions, and could comprise different materials or cross sections. Suitable materials for the surrounding material include those listed above for the tube embodiment of FIGS. 16A and 16B. Various braids or weaves including the magnetic material in wire form could also be envisaged within the scope of the invention.

In any of the above embodiments, the marker may comprise a resiliently deformable member (tube, wire strands or coating) containing the LBJ wire such that the coil expands on deployment to a larger size. The expansion may be driven elastically by a resiliently deformable material or by a shape memory transition material such as nitinol.

Figure 18A:
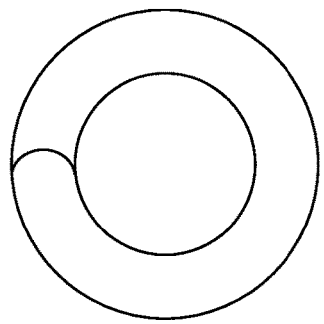
FIGS. 18A to 18C illustrate examples of possible cross-sections for a marker according to the present invention.
Figure 18B:
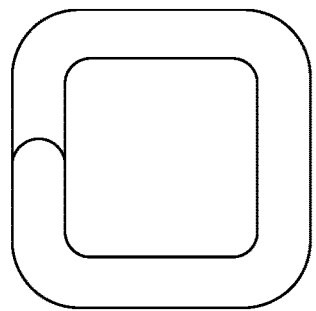
Figure 18C:
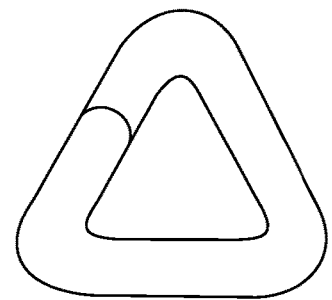

In a further embodiment, the cross section of the marker may take a number of forms including round, rectangular or triangular, as shown in FIGS. 18A to 18C respectively. In certain instances, a marker having a section in which there is a substantially straight side (such as in FIGS. 18B and 18C) may be advantageous in order to provide angles at which there is an increased magnetic response relative to other angles, e.g. when a straight section is aligned with the excitation field.

Table 1 below illustrates characteristics of markers according to the invention and their H3 magnetic response. Embodiments shown in FIGS. 6 to 10 of the drawings are identified in column 1.

TABLE 1

| Marker | Diameter (mm) | Length (mm) | Number of Turns | Pitch (mm) | Aspect ratio (length:diameter) | Ratio max:min H3 magnetic response | Dominant Direction | Housing Material |
|---|---|---|---|---|---|---|---|---|
| Prior Art straight length of wire | 0.1 | 4 | none | N/A | 40.0 | 39.1 | Axial | None |
| Single Coil | 1.26 | 7 | 22 | 0.32 | 5.6 | 19.8 | Perp. | Cu |
| Single Coil | 1.26 | 7 | 11 | 0.64 | 5.6 | 6.6 | Perp. | Cu |
| Single Coil | 1.26 | 7 | 8 | 0.88 | 5.6 | 5.5 | Perp. | Cu |
| Single Coil | 1.26 | 7 | 4.5 | 1.56 | 5.6 | 1.4 | None | Cu |
| Single Coil | 1.06 | 8 | 1.5 | 5.3 | 7.5 | 4.7 | Axial | Cu |
| Single Coil | 1.16 | 6 | 2 | 3.0 | 5.2 | 1.6 | None | Cu |
| Single Coil (FIG. 6A) | 1.03 | 6 | 17 | 0.35 | 5.8 | 10.9 | Perp. | Cu |
| Coil & Axial wire (FIG. 6B) Coil:Axial wire: | 1.03 0.1 | 6 3.2 | 17 none | 0.35 N/A | 5.8 | 1.2 | None | Cu None |
| Single Coil (FIG. 7B) | 1.01 | 7 | 8.5 | 0.82 | 5.6 | 1.2 | None | Ti |
| Variable Pitch Coil (FIG. 8A) | 1.01 | 8 | 1 9 1 | 2.5 0.33 2.5 | 7.9 | 2.2 | Perp. | Cu |
| Mullti-coil, 3 coils (FIG. 10B) | 1.06 | 7 | 3 × 3 | 2.33 | 6.6 | 1.6 | None | Cu |

Table 2 below illustrates the effect of the housing material of the marker on the magnitude of H3 response at a distance of 20 mm for a probe of a straight length of Co—Fe LBJ material of 4 mm.

TABLE 2

| Housing Material | Hosing Diameter (mm) | Housing Length (mm) | Housing Material Resistivity (Ωm) | H3 response relative to copper | Ratio max:min H3 magnetic response |
|---|---|---|---|---|---|
| Copper | 0.29 | 4 | $1.7 \times 10^{-8}$ | 1 | 3 |
| 316 Stainless Steel | 0.50 | 4 | $7.4 \times 10^{-7}$ | 16 | 23 |

TABLE 2-continued

| Housing Material | Hosing Diameter (mm) | Housing Length (mm) | Housing Material Resistivity (Ωm) | H3 response relative to copper | Ratio max:min H3 magnetic response |
|---|---|---|---|---|---|
| Titanium | 0.51 | 4 | $5.2 \times 10^{-7}$ | 17 | 26 |
| Nitinol | 0.33 | 4 | $7.6 \times 10^{-7}$ | 19 | 41 |

Table 3 below shows how the magnitude of H3 response varies with diameter at a distance of 20 mm for a marker with similar coil pitches for coils in both 304ss and PET as well as demonstrating the increased response from coils in a material where there is less opposing eddy currents e.g. coils (PET), showing the increase in relative response per turn for the single coils with diameter. It also demonstrates the increased signal from a coil of smaller diameter inside a coil of larger diameter (FIG. 14). All coils are measured in a perpendicular orientation.

TABLE 3

| Coil | Coil Material | Magnetic Material Diameter (mm) | Coil Length (mm) | No of Turns | Pitch (mm) | Signal per Turn/ 304 ss ø0.88 mm Signal per turn | H3 response relative ø0.88 mm 304 ss coil |
|---|---|---|---|---|---|---|---|
| Single Coil A | 304 ss | 0.88 | 5 | 13 | 0.39 | 1 | 1 |
| Single Coil E | 304 ss | 0.99 | 7 | 17 | 0.41 | 1.8 | 2.3 |
| Single Coil B | 304 ss | 1.10 | 5 | 14 | 0.36 | 2.9 | 3.1 |
| Single Coil C | 304 ss | 1.25 | 5 | 14 | 0.36 | 3.3 | 3.5 |
| Single Coil D | 304 ss | 2.02 | 5 | 11.5 | 0.43 | 6.2 | 5.5 |
| Coil C inside Coil D (9) | 304 ss | 1.25 inside 2.02 | 5 | 14 inside 11.5 | 0.36 inside 0.43 | N/A | 6.7 |
| Single Coil F | PET | 1.1 | 8 | 15 | 0.53 | 3.9 | 4.5 |
| Single Coil G | PET | 1.2 | 6 | 10 | 0.60 | 4.6 | 3.5 |
| Single Coil H | PET | 1.46 | 5.8 | 10 | 0.58 | 5.9 | 4.5 |
| Single Coil I | PET | 2.22 | 5.4 | 10 | 0.54 | 7.7 | 5.9 |
| Single Coil J | PET | 3.26 | 5.8 | 10 | 0.58 | 10.1 | 7.8 |

FIGS. 19A to 19D show how the response of various markers varies with the orientation of the marker axis relative to the detection probe, when the marker is excited with the probe arrangement of FIG. 1. In each case the long axis of the marker is aligned with the 0-180° axis in the figure.

Figure 19A:
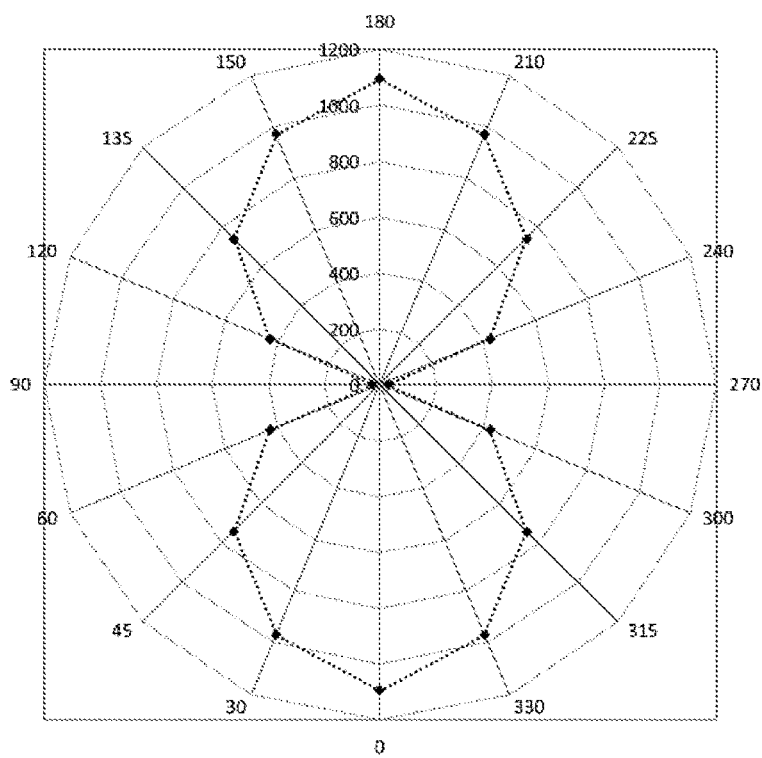
FIG. 19A illustrates the harmonic response for a marker according to the prior art, with the wire lying along the 0-180° axis in the chart.

FIG. 19A shows the magnetic response from a prior art single cobalt-iron amorphous LBJ microwire. The harmonic (e.g. H3) response is stronger by a factor of almost 40 times in the axial direction versus the transverse direction of sensing. This asymmetry of response would be expected from a straight length of LBJ wire based on the prior art literature, for example von Gutfeld (von Gutfeld, R J et al., Amorphous magnetic wires for medical locator applications, Appl. Phys. Lett., Vol. 81, No. 10, 2 Sep. 2002) which describes an axial response many times stronger than the transverse response.

Figure 19B:
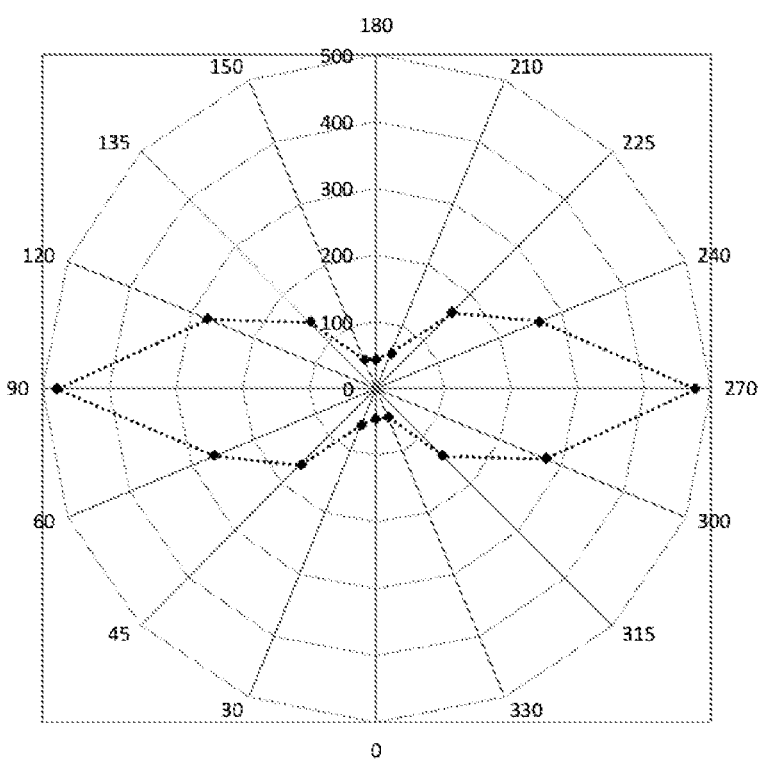
FIG. 19B illustrates the harmonic response from the marker shown in FIG. 6A, with the wire lying along the 0-180° axis in the chart.

FIG. 19B shows the magnetic response from the marker of FIG. 6A constructed with a cobalt-iron amorphous LBJ microwire wherein the LBJ wire is in the form of a coil. According to the conventional theory, LBJ wires need to be straight to produce a harmonic response. However, surprisingly, for a piece of LBJ wire, the coil produces a strong harmonic response. More surprisingly, the transverse harmonic response is stronger than the axial harmonic response which is contrary to what would be expected from the physical aspect ratio (length:diameter) which in this case is approximately 6 (see Table 1).

The inventors have found that such markers can be combined to create a marker with a more optimal or preferred harmonic response profile. Specifically, it is preferable if the harmonic response at a given distance from the marker is substantially uniform.

Thus for example, the prior art single straight wire can be combined with the coil of FIG. 6A, to obtain the marker of FIG. 6B.

Figure 19C:
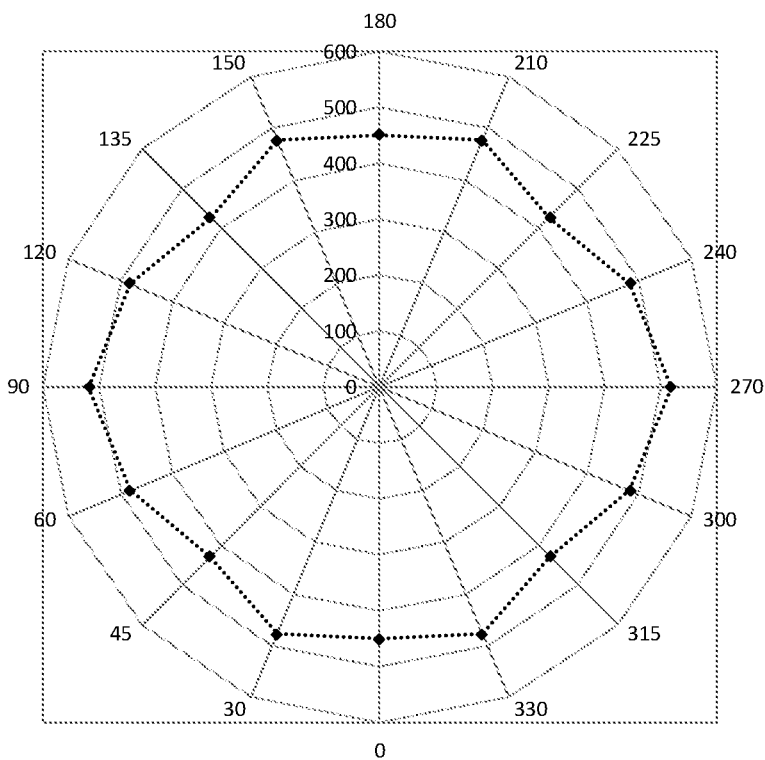
FIG. 19C illustrates the harmonic response from the marker shown in FIG. 6B, with the wire lying along the 0-180° axis in the chart.

FIG. 19C shows the variation in the harmonic (H3) response from such a marker of FIG. 6B, constructed with a cobalt-iron amorphous LBJ microwire, as its orientation with respect to the probe is varied. The marker comprises a coil of fine copper tube containing cobalt-iron amorphous LBJ microwire as the magnetic material, the tube being wound into a coil with a further length of the same LBJ wire positioned axially inside the coil. The coil is 1.03 mm in diameter, 6 mm long and has 17 turns, giving a pitch of 0.35 mm. The axial wire is 3.2 mm long.

It is demonstrated in FIG. 19C that the harmonic magnetic response is substantially uniform regardless of the direction of detection, and specifically, the H3 response in the axial direction is similar to that in the transverse direction. Thus by appropriate choice of coil parameters and choice of additional axial components, the uniformity of the harmonic response can be adjusted and optimised to obtain the profile of response versus direction that is desired. This could be increased transverse response or axial response, but is most preferably a uniform or equal response regardless of the direction of excitation or sensing. The advantage of a uniform response is that the signal can be reliably and consistently converted into a distance measurement from the probe to the marker. If the uniformity is poor, the user will obtain a different distance measurement depending on the orientation of the marker with respect to the probe which would be confusing. The uniformity of response can be estimated by measuring the variation of response with orientation of the marker relative to the probe, and calculating the ratio of the maximum to minimum response.

In the context of this disclosure, a uniform response means that the ratio of the maximum to minimum magnitude of the response being measured (be it H3, or other magnetic response) is less than 3 and preferably less than 2. Because the magnetic response when being detected with an arrangement similar to that in FIG. 1 drops off with between the third and fifth power of distance, if the ratio of maximum to minimum magnetic response is less than 2, then the variation in measured distance as the orientation of the marker changes will be within a small range, typically less than ±1-2 mm.

Figure 20:
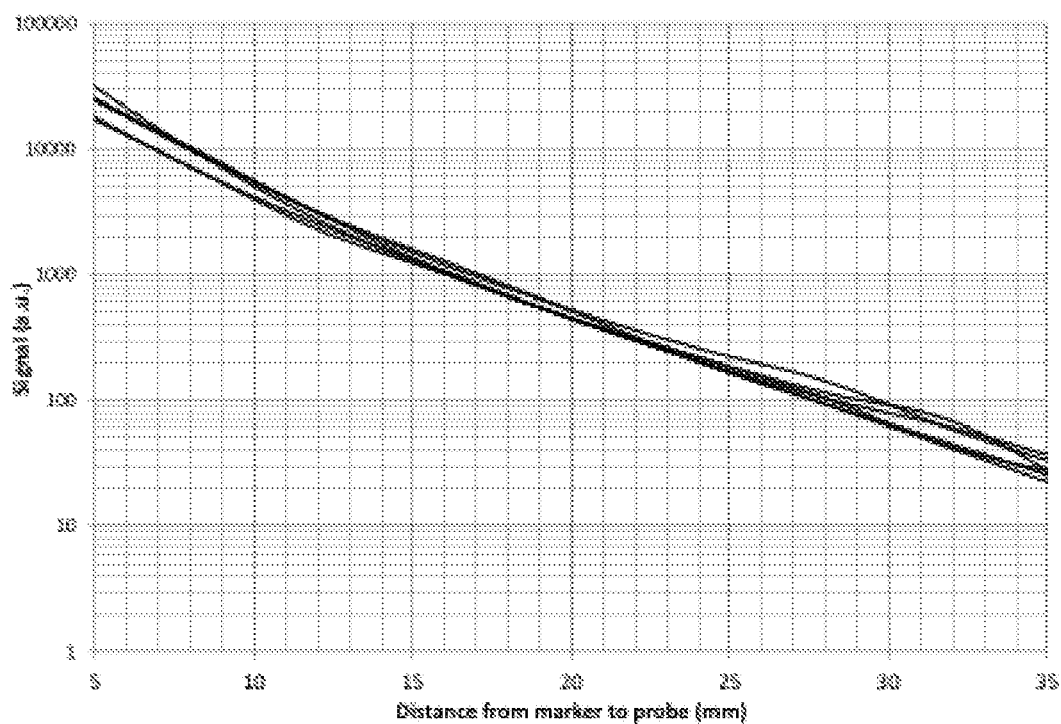
FIG. 20 illustrates the marker magnetic H3 response with distance from a probe for the marker of FIG. 7B, wherein each line is one orientation, and orientations of 0, 30, 45, 60 and 90 degrees to the long axis of the marker are shown.

FIG. 20 shows plots of H3 magnetic response versus distance (using the configuration of FIG. 1) for the marker of FIG. 7B for a number of orientations of the marker. This illustrates how the accuracy of the distance determination can be maintained within ±1-2 mm regardless of orientation of the marker relative to the probe. Table 1 above shows the max:min ratio of H3 response for a range of markers of different constructions.

The uniformity of response can also be varied by adjusting the pitch, number of turns/convolutions, length, diameter, shape, cross section and end configuration of the coil, and by varying the diameter or pitch of the turns at different points along the length of the coil.

Figure 19D:
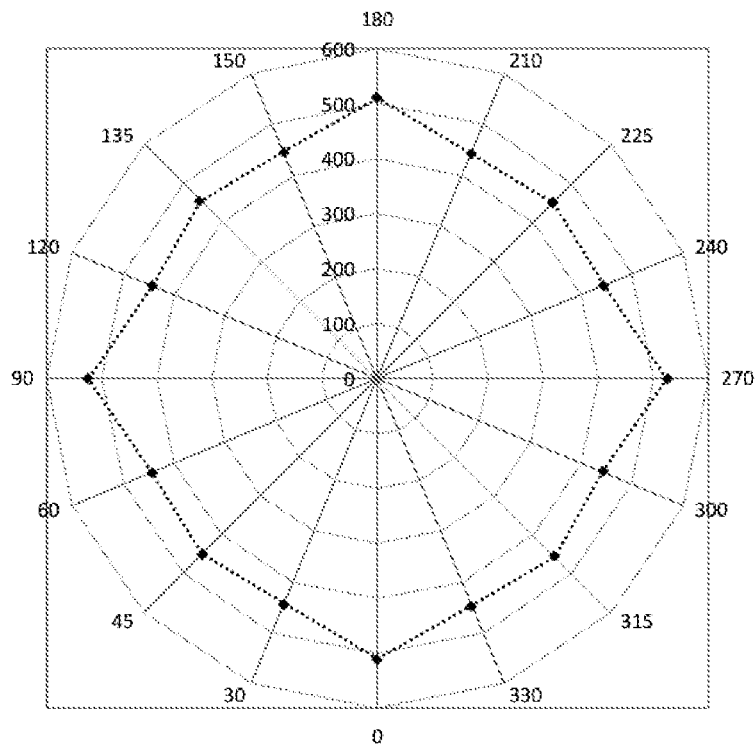
FIG. 19D illustrates the harmonic response from the marker of FIG. 7B, with the wire lying along the 0-180° axis in the chart.

FIG. 19D shows the response from the embodiment of FIG. 7B which has an increased pitch. The marker comprises a coil of cobalt-iron amorphous LBJ microwire with length 7 mm, diameter 1.01 mm, and 8.5 turns giving a pitch of 0.82 mm.

By increasing the pitch compared with the marker of FIG. 6A, the axial harmonic (H3) response can be increased with respect to the transverse harmonic to make the response substantially uniform, regardless of the direction of sensing. In this case the max:min ratio of the H3 response is 1.2.

If the pitch is increased to improve the uniformity of the response, the length of the marker for a given magnitude of response will increase, or the number of convolutions in a given length of marker will be reduced. The inventors have found that in this case, more than one coil can be combined in the form of a multi-start helix to increase the response while maintaining the small size of the marker. FIGS. 10A and 10B show two such examples, one with 2 and one with 3 coils respectively, combined within the marker. In these examples the pitches of the combined coils are the same, but it is to be appreciated that the pitch of the combined coils could be varied to obtain the desired profile of response.

The present invention provides a new and improved magnetic marker that may be used in a system and method for detecting the marker, thereby enabling a lesion for surgical excision to be located. The marker contains at least a piece of LBJ magnetic material that is wound into a coil having at least one, preferably more, convolutions. The marker may be excited at the switching field (bistable mode) or at a field lower than the bistable switching field (sub-bistable mode) and the generated harmonics measured from any direction to determine the position and orientation of the marker. In embodiments, the marker may also be provided below the critical length of the LBJ material required to enable bistable switching behaviour.

The invention claimed is:
1. A magnetic marker comprising:
   at least one implantable marker, the implantable marker comprising at least one piece of magnetic material that exhibits a large Barkhausen jump (LBJ) in its magnetisation curve, wherein the magnetic material comprises at least one overlapping loop, the at least one overlapping loop being retained in the implantable marker during detection of the marker following implantation.

2. A magnetic marker as claimed in claim 1, wherein the implantable marker comprises at least one piece of LBJ material having at least two full convolutions to form a coil or helix.

3. A magnetic marker as claimed in claim 2, wherein the at least two full convolutions have a uniform pitch.

4. A magnetic marker as claimed in claim 2, wherein the at least two full convolutions have a variable pitch.

5. A magnetic marker as claimed in claim 2, wherein the at least two full convolutions have a uniform diameter.

6. A magnetic marker as claimed in claim 2, wherein the at least two full convolutions have a variable diameter.

7. A magnetic marker as claimed in claim 1 wherein the implantable marker includes at least one axial member comprising at least one piece of LBJ material extending at least partially through the at least one loop of the marker.

8. A magnetic marker as claimed in claim 7, wherein the at least one axial member is in the form of a separate piece of material inserted through the at least one loop or is formed integrally with the at least one loop at one or both ends of the implantable marker.

9. A magnetic marker as claimed in claim 1 comprising multiple coils wherein the multiple coils are combined in the form of a multi-start helix.

10. A magnetic marker as claimed in claim 1 comprising multiple coils wherein at least one coil having convolutions of a smaller diameter is contained within at least one coil having convolutions of a relatively larger diameter.

11. A magnetic marker as claimed in claim 1, wherein the magnetic material is coated with a coating or provided within a housing, the coating or housing having a relatively low conductivity.

12. A magnetic marker as claimed in claim 11 wherein the coating or housing is formed from a material having a resistivity greater than $2 \times 10^{-7}$ $\omega$m.

13. A magnetic marker as claimed in claim 11 wherein the implantable marker is provided within a housing of Nitinol, titanium, stainless steels or other biocompatible alloys.

14. A magnetic marker as claimed in claim 11 wherein the implantable marker includes a housing comprising one or more strands of material which are wound around the magnetic material.

15. A magnetic marker as claimed in claim 14, wherein the housing is in the form of a helix.

16. A detection system for locating a marker, the system comprising: a magnetic marker, the magnetic marker comprising at least one implantable marker, the implantable marker comprising at least one piece of magnetic material that exhibits a large Barkhausen jump (LBJ) in its magnetisation curve, wherein the magnetic material comprises at least one overlapping loop, said at least one overlapping loop being retained in the at least one implantable marker during detection of the marker following implantation;

at least one drive coil arranged to excite the marker with an alternating magnetic field and at least one sense coil arranged to detect a signal received from an excited marker;

a magnetic field generator arranged to drive an alternating magnetic field through the at least one drive coil; and at least one detector arranged to receive the signal from the sense coil and detect one or more harmonics of a drive frequency in received signal.

17. A detection system according to claim 16 wherein the drive coil is configured to excite the marker to above its switching field to initiate bistable switching behaviour of the LBJ material.

18. A detection system as claimed in claim 16, wherein the at least one drive coil is configured to excite the marker below the switching field required to initiate bistable switching behaviour of the LBJ material of the marker.

19. A detection system according to claim 18 wherein the ratio of maximum to minimum harmonic response of the marker is <3.

20. A detection system according to claim 16 wherein the at least one detector detects a harmonic response of the marker to determine location/distance/proximity of the marker from a probe.

* * * * *